US008815304B2

(12) United States Patent
Forbes

(10) Patent No.: US 8,815,304 B2
(45) Date of Patent: Aug. 26, 2014

(54) COMPOSITIONS AND METHODS FOR PROMOTING APPETITE SUPPRESSION USING ALKALI METALS

(75) Inventor: Arnold Forbes, Reunion (FR)

(73) Assignee: Ashberry International Limited, Road Town (VG)

( * ) Notice: Subject to any disclaimer, the term of this patent is extended or adjusted under 35 U.S.C. 154(b) by 316 days.

(21) Appl. No.: 13/075,904

(22) Filed: Mar. 30, 2011

(65) Prior Publication Data

US 2011/0244055 A1  Oct. 6, 2011

(30) Foreign Application Priority Data

Apr. 1, 2010 (EP) .................................. 10290187

(51) Int. Cl.
*A61K 33/14* (2006.01)
*A23L 1/30* (2006.01)
*A23L 1/304* (2006.01)
*A23L 2/38* (2006.01)

(52) U.S. Cl.
CPC ............... *A23L 1/304* (2013.01); *A23L 1/3002* (2013.01); *A61K 33/14* (2013.01); *A23V 2002/00* (2013.01)
USPC ............... 424/722; 424/677; 426/72; 426/74; 426/590

(58) Field of Classification Search
None
See application file for complete search history.

(56) References Cited

U.S. PATENT DOCUMENTS

| 4,322,407 | A  | * | 3/1982 | Ko ................................ 424/601 |
| 6,011,061 | A  |   | 1/2000 | Lai |
| 7,429,580 | B2 |   | 9/2008 | Gadde et al. |
| 2002/0064566 | A1 | * | 5/2002 | Beckett ......................... 424/686 |
| 2006/0008908 | A1 | * | 1/2006 | Giles ............................. 435/455 |
| 2006/0160750 | A1 | * | 7/2006 | Krishnan et al. ................ 514/23 |

FOREIGN PATENT DOCUMENTS

| AU | 20464/88 | 2/1989 |
| EP | 0305097 A2 | 3/1989 |
| WO | 02/069955 A1 | 9/2002 |
| WO | 2006/014578 A2 | 2/2006 |
| WO | 2008/140444 A1 | 11/2008 |

OTHER PUBLICATIONS

Schrauzer et al., Lithium:Occurrence, Dietary Intakes, Nutritional Essentiality, Journal of the American College of Nutrition (2002), vol. 21, No. 1, pp. 14-21.*
Smith et al., Lithium in the brines of Fish Lake Valley and Columbus Salt Marsh, Nevada, United States Department of the Interior Geological Survey (1977), pp. 1-22.*
Casacchia et al., Rubidium Chloride in Chronic Mood Disorders, Recurrent Mood Disorders (1993), pp. 286-290.*
PUBMED online, file MEDLINE, PMID 6522428 (Neulieb, Effect of oral intake of cesium chloride: a single case report, Pharmacol. Biochem. Behav. (1984), vol. 21 Suppl. 1, pp. 15-16), Abstract.*
Beck et al., Studies on the mechanism of rubidium-induced kaliuresis, Kidney International, 36:175-182 (1989).
Kazes et al., Eating Behaviour and Long-Term Lithium Treatment, Lithium, 4:125-133 (1993).
Search Report for European Patent Appl. No. 10290187.3, mailed May 31, 2011, European Patent Office.

* cited by examiner

*Primary Examiner* — Abigail Fisher
*Assistant Examiner* — Frank Choi
(74) *Attorney, Agent, or Firm* — Nevrivy Patent Law Group P.L.L.C.

(57) ABSTRACT

The present invention relates to a method of suppressing appetite or promoting a stimulant effect in an individual in need thereof, comprising administering to the individual per 24 hour period an effective amount of one or more alkali metals selected from the group consisting of one or more sources of cesium, one or more sources of rubidium, one or more sources of lithium, and combinations thereof. The present invention further relates to weight loss or stimulant compositions comprising one or more alkali metals.

19 Claims, No Drawings

COMPOSITIONS AND METHODS FOR PROMOTING APPETITE SUPPRESSION USING ALKALI METALS

BACKGROUND OF THE INVENTION

1. Field of the Invention

The field of the invention relates to weight loss, obesity and appetite suppression, more particularly, to methods of suppressing appetite by administering one or more alkali metals to an individual in need thereof.

2. Description of the Related Art

Obesity is fast becoming an acute global health crisis, particularly in the developed world. About 97 million adults in the United States are overweight or obese and the problem is growing in Europe and Asia as well. The medical problems caused by being overweight or obese can be serious and often life-threatening, and include diabetes, shortness of breath, gallbladder disease, hypertension, elevated blood cholesterol levels, cancer, arthritis, other orthopedic problems, reflux esophagitis (heartburn), snoring, sleep apnea, menstrual irregularities, infertility and heart trouble. Moreover, obesity or being overweight substantially increases the risk of morbidity from hypertension, dyslipidemia, type 2 diabetes, coronary heart disease, stroke, gallbladder disease, osteoarthritis and endometrial, breast, prostate, and colon cancers. Higher body weights are also associated with increases in all-cause mortality. Most or all of these problems are relieved or improved by permanent significant weight loss. Longevity and quality of life is likewise significantly increased by permanent significant weight loss.

Excessive weight and/or obesity may be due to uncontrollable and/or controllable factors. Uncontrollable factors may include heredity (i.e., genetics) and metabolic disorders. Controllable factors may include environment, physical inactivity, psychological circumstances, and poor eating habits established in childhood and use of certain medications. Poor eating habits may include excessive intake as well as poor selection of foods with nutritional value. The controllable factors are often more responsible for the development of overweight and obesity.

Therapeutic approaches to overweight and obesity have included educational, physical, psychological and pharmacological modalities. Educational efforts have focused on informing individuals about caloric intake and making proper nutritional selections. Physical approaches have emphasized increasing physical activity in an effort to increase metabolism. Psychological approaches have focused on controlling appetite, manipulating mood and improving sense of well-being. Pharmacological approaches may include drugs and other agents to suppress appetite and/or increase cellular metabolism. There are a broad range of opinions as to how successful these therapeutic approaches have been either individually or collectively, but nevertheless, incidence and prevalence of overweight and obesity continue to increase. Regardless of cause, there is an obvious need for treatments that can induce or otherwise promote weight loss.

Accordingly, there exists a need for new, effective weight loss treatments which are accompanied by few adverse or undesirable side effects or less serious side effects. In particular, there exists a need for developing weight loss treatments which can potentially lower major endpoints such as death and/or myocardial infarction rates by directly treating obesity rather than treating the consequences of obesity (e.g., diabetes, hypertension, hyperlipidemia), as is currently the practice.

BRIEF SUMMARY OF THE INVENTION

The above and other objectives, as will be apparent to those having ordinary skill in the art, have been achieved by the present inventor by providing methods for suppressing appetite using one or more alkali metals.

More specifically, in one aspect, the invention provides a method for suppressing appetite in an individual in need thereof, comprising administering to the individual per 24 hour period an effective amount of one or more alkali metals selected from the group consisting of one or more sources of cesium, one or more sources of rubidium, one or more sources of lithium, and combinations thereof.

The invention advantageously provides convenient and safe methods for suppressing appetite and thereby achieving weight loss in an individual. Being overweight or obese poses major health risks for individuals, and methods described herein are highly beneficial in that numerous associated diseases and attendant conditions due to being overweight or obese can be prevented or ameliorated. This, in turn, can prevent pain, suffering, and even death caused by being overweight or obese as well as significantly reduce health care costs associated with being overweight or obese. The methods disclosed herein also advantageously improve mood and energy level, and enhance an individual's overall sense of well being. The methods can also eliminate or reduce the need for weight reduction surgery, such as, for example, liposuction or gastric bypass surgery. Furthermore, the methods disclosed herein may advantageously be employed by a normal weight individual to suppress appetite (for foods that induce weight gain rapidly such as "junk" food) and prevent a significant gain in weight under various circumstances.

In another aspect, the invention encompasses weight loss compositions useful for suppressing appetite in an individual. The compositions comprise one or more alkali metals useful in carrying out the methods of the present invention as described herein.

In another aspect, the invention is directed to methods of promoting a stimulant effect, such as enhancing energy, attentiveness, or improving athletic performance in an individual in need thereof, comprising administering to the individual an effective amount of one or more alkali metals selected from the group consisting of one or more sources of cesium, one or more sources of rubidium, one or more sources of lithium, and combinations thereof.

In another aspect, the invention encompasses beverage compositions useful, for example, as energy or stimulant drinks, comprising one or more alkali metals selected from the group consisting of one or more sources of cesium, one or more sources of rubidium, one or more sources of lithium, and combinations thereof.

DETAILED DESCRIPTION OF THE INVENTION

In some embodiments, the invention is directed to methods and compositions for suppressing appetite in an individual in need thereof. In some embodiments, the methods comprise administering to the individual per 24 hour period an effective amount of one or more alkali metals selected from the group consisting of one or more sources of cesium, one or more sources of rubidium, one or more sources of lithium, and combinations thereof.

The compositions of the invention useful for suppressing appetite are also useful for other purposes. For example, the compositions are useful in promoting a stimulant effect, such as enhancing energy, attentiveness, and improving athletic performance in an individual in need thereof. In some embodiments, the invention is directed to methods of promoting a stimulant effect, such as enhancing energy, attentiveness, or improving athletic performance in an individual in need thereof, comprising administering to the individual an effective amount of one or more alkali metals selected from the group consisting of one or more sources of cesium, one or more sources of rubidium, one or more sources of lithium, and combinations thereof.

The phrase "effective amount" as used herein refers to the amount of an alkali metal or combinations thereof of the invention which is effective for producing the desired appetite suppressant or stimulant effect upon administration to an individual or patient. The desired appetite suppressant effect is sufficient to either promote weight loss in an individual or prevent weight gain in a normal weight individual who otherwise might be at risk for weight gain, for example, as might occur when the individual is being treated with certain medications which promote weight gain due to increased appetite as a side effect, or individuals who have a propensity to consume foods high in fats or who otherwise have a nutritionally poor diet or eating habits. The amount of weight loss that can be achieved in an individual can range from about 1 kg to about 150 kg or more. In some embodiments, the amount of weight loss that can be achieved is about 5 kg, 10 kg, 15 kg, 20 kg, 25 kg, 30 kg, 35 kg, 40 kg 45 kg or 50 kg. On a percentage basis, in general, the amount of weight that can be lost can range from about 1% of the individual's body weight up to about 70% or more of the individual's weight. High percentage losses in body weight are possible for very obese individuals and should only occur under proper medical supervision. The word "about" as used herein corresponds to ±10%.

In some embodiments, the source of cesium administered has total cesium content in an amount of about 40 milligrams to about 1500 milligrams. In some embodiments, the source of cesium administered has total cesium content that ranges from about 40-1250 milligrams, from about 40-1000 milligrams, from about 40-750 milligrams, from about 60-500 milligrams, from about 80-400 milligrams, from about 100-300 milligrams, or from about 150-250 milligrams. In some embodiments, the total cesium content is about 40 milligrams, about 50 milligrams, about 60 milligrams, about 75 milligrams, about 100 milligrams, about 150 milligrams, about 200 milligrams, about 250 milligrams, about 300 milligrams, about 350 milligrams, about 400 milligrams, about 450 milligrams, about 500 milligrams, about 550 milligrams, about 600 milligrams, about 650 milligrams, about 700 milligrams, about 750 milligrams, about 800 milligrams, about 850 milligrams, about 900 milligrams, about 950 milligrams, about 1000 milligrams, about 1050 milligrams, about 1100 milligrams, about 1200 milligrams, about 1250 milligrams, about 1300 milligrams, about 1350 milligrams, about 1400 milligrams, about 1450 milligrams, or about 1500 milligrams.

In some embodiments, the source of cesium is elemental cesium, one or more cesium compounds, cesium ions, salts of cesium, or combinations thereof. In some embodiments, the source is one or more salts of cesium having total cesium content in an amount of about 40 milligrams to about 1500 milligrams. In some embodiments, the one or more salts of cesium is selected from the group consisting of cesium azide ($CsN_3$), cesium bromide (CsBr), cesium carbonate ($Cs_2CO_3$), cesium chloride (CsCl), cesium chromate ($Cs_2CrO_4$), cesium fluoride (CsF), cesium formate (HCOOCs), cesium iodide (CsI), cesium nitrate ($CsNO_3$), cesium orthovanadate ($Cs_3VO_4$), cesium oxalate (($COOCs)_2$), cesium perchlorate ($CsClO_4$), cesium permanganate ($CsMnO_4$), cesium propionate ($C_2H_5CO_2Cs$) and cesium sulfate ($Cs_2O_4S$).

In some embodiments, the salt of cesium is cesium chloride and the salt is administered in an amount of about 50 milligrams to about 1900 milligrams (total cesium content of about 40 to about 1500 milligrams). In some embodiments, the salt is administered in an amount of about 50-1700 milligrams, from about 50-1500 milligrams, from about 50-1200 milligrams, from about 75-1000 milligrams, from about 100-800 milligrams, from about 200-600 milligrams, or from about 300-500 milligrams. In some embodiments, about 50 milligrams, about 75 milligrams, about 100 milligrams, about 200 milligrams, about 300 milligrams, about 400 milligrams, about 500 milligrams, about 600 milligrams, about 700 milligrams, about 800 milligrams, about 900 milligrams, about 1000 milligrams, about 1100 milligrams, about 1200 milligrams, about 1300 milligrams, about 1400 milligrams, about 1500 milligrams, about 1600 milligrams, about 1700 milligrams, about 1800 milligrams or about 1900 milligrams of cesium chloride is administered.

In some embodiments, the source of rubidium has total rubidium content in an amount of about 35 milligrams to about 1350 milligrams. In some embodiments, the source of rubidium administered has total rubidium content that ranges from about 35-1250 milligrams, from about 35-1000 milligrams, from about 35-750 milligrams, from about 50-500 milligrams, from about 80-400 milligrams, from about 100-300 milligrams, or from about 150-250 milligrams. In some embodiments, the total rubidium content is about 35 milligrams, about 45 milligrams, about 50 milligrams, about 70 milligrams, about 90 milligrams, about 100 milligrams, about 150 milligrams, about 200 milligrams, about 250 milligrams, about 300 milligrams, about 350 milligrams, about 400 milligrams, about 450 milligrams, about 500 milligrams, about 550 milligrams, about 600 milligrams, about 650 milligrams, about 700 milligrams, about 750 milligrams, about 800 milligrams, about 850 milligrams, about 900 milligrams, about 950 milligrams, about 1000 milligrams, about 1050 milligrams, about 1100 milligrams, about 1200 milligrams, about 1250 milligrams, about 1300 milligrams, or about 1350 milligrams.

In some embodiments, the source of rubidium is elemental rubidium, one or more rubidium compounds, rubidium ions, salts of rubidium, or combinations thereof. In some embodiments, the one or more sources of rubidium are one or more salts of rubidium. In some embodiments, the total content of rubidium in the one or more salts of rubidium is in an amount of about 35 milligrams to about 1350 milligrams. In some embodiments, the one or more salts of rubidium is selected from the group consisting of rubidium acetate ($CH_3CO_2Rb$), rubidium bromide (RbBr), rubidium carbonate ($Rb_2CO_3$), rubidium chloride (RbCl), rubidium chromate ($Rb_2CrO_4$), rubidium fluoride (RbF), rubidium formate ($HCO_2Rb$), rubidium iodide (RbI), rubidium nitrate ($RbNO_3$) and rubidium sulfate ($Rb_2SO_4$). In some embodiments, the salt of rubidium is rubidium chloride.

In some embodiments, rubidium chloride is administered in an amount of about 50 milligrams to about 1900 milligrams (total rubidium content of about 35 milligrams to about 1350 milligrams). In some embodiments, the salt is administered in an amount of about 50-1700 milligrams, from about 50-1500 milligrams, from about 50-1200 milligrams, from about 75-1000 milligrams, from about 100-800 milligrams, from about 200-600 milligrams, or from about 300-500 milligrams. In some embodiments, about 50 milligrams, about 60 milligrams, about 70 milligrams, about 75 milligrams, about 90 milligrams, about 100 milligrams, about 200 milligrams, about 300 milligrams, about 400 milligrams, about 500 milligrams, about 600 milligrams, about 700 milligrams, about 800 milligrams, about 900 milligrams, about 1000 milligrams, about 1100 milligrams, about 1200 milligrams, about 1300 milligrams, about 1400 milligrams, about 1500 milligrams, about 1600 milligrams, about 1700 milligrams, about 1800 milligrams or about 1900 milligrams of rubidium chloride is administered.

In some embodiments, the source of lithium has a total lithium content in an amount of about 0.3 milligrams to about 85 milligrams. In some embodiments, the source of lithium administered has total lithium content that ranges from about 0.3-80 milligrams, from about 0.3-70 milligrams, from about 0.3-50 milligrams, from about 1-40 milligrams, from about 3-35 milligrams, from about 5-30 milligrams, or from about 10-20 milligrams. In some embodiments, the total lithium content is about 0.5 milligrams, about 1 milligrams, about 5 milligrams, about 10 milligrams, about 15 milligrams, about 20 milligrams, about 25 milligrams, about 30 milligrams, about 35 milligrams, about 40 milligrams, about 45 milligrams, about 50 milligrams, about 55 milligrams, about 60 milligrams, about 65 milligrams, about 70 milligrams, about 75 milligrams, about 80 milligrams, or about 85 milligrams. In some embodiments, the one or more sources of lithium is elemental lithium, one or more lithium compounds, lithium ions, lithium salts, or combinations thereof.

In some embodiments, the source of lithium is one or more lithium salts. In some embodiments, the total content of lithium in one or more lithium salts is in an amount of about 0.3 milligrams to about 85 milligrams. In some embodiments, the one or more lithium salts is selected from the group consisting of lithium acetate ($CH_3COOLi$), lithium acetylsalicylate, lithium aspartate, lithium benzoate ($C_6H_5COOLi$), lithium bitartrate, lithium bromide (LiBr), lithium carbonate ($Li_2CO_3$), lithium chloride (LiCl), lithium chromate ($LiCrO_4$), lithium citrate ($Li_3C_6H_5O_7$), lithium fluoride (LiF), lithium gluconate, lithium iodate ($LiIO_3$), lithium metaborate ($LiBO_2$), lithium nitrate ($LiNO_3$), lithium orotate ($LiC_5H_3N_2O_4$), lithium perchlorate ($LiClO_4$), lithium phosphate ($Li_3PO_4$), lithium selenite ($LiH_3(SeO_3)_2$), lithium succinate ($C_4H_5LiO_4$), lithium sulfate ($Li_2SO_4$), and lithium thenoate. In some embodiments, the one or more lithium salts is lithium aspartate, lithium carbonate, lithium citrate or lithium orotate, or combinations thereof.

In some embodiments, the source of lithium is lithium carbonate administered in an amount of about 10 milligrams to about 450 milligrams. In some embodiments, lithium carbonate is administered in an amount of about 10-400 milligrams, from about 15-350 milligrams, from about 20-300 milligrams, from about 50-250 milligrams, from about 75-200 milligrams, from about 100-200 milligrams, or from about 125-175 milligrams. In some embodiments, about 10 milligrams, about 15 milligrams, about 20 milligrams, about 25 milligrams, about 30 milligrams, about 35 milligrams, about 40 milligrams, about 45 milligrams, about 50 milligrams, about 75 milligrams, about 100 milligrams, about 150 milligrams, about 200 milligrams, about 250 milligrams, about 300 milligrams, about 350 milligrams, about 400 milligrams, or about 450 milligrams lithium carbonate is administered.

In some embodiments, the source of lithium is lithium aspartate and is administered in an amount of about 10 milligrams to about 450 milligrams. In some embodiments, lithium aspartate is administered in an amount of about 10-400 milligrams, from about 15-350 milligrams, from about 20-300 milligrams, from about 50-250 milligrams, from about 75-200 milligrams, from about 100-200 milligrams, or from about 125-175 milligrams. In some embodiments, about 10 milligrams, about 15 milligrams, about 20 milligrams, about 25 milligrams, about 30 milligrams, about 35 milligrams, about 40 milligrams, about 45 milligrams, about 50 milligrams, about 75 milligrams, about 100 milligrams, about 150 milligrams, about 200 milligrams, about 250 milligrams, about 300 milligrams, about 350 milligrams, about 400 milligrams, or about 450 milligrams lithium aspartate is administered.

In some embodiments, the source of lithium is lithium citrate administered in an amount of about 10 milligrams to about 450 milligrams. In some embodiments, lithium citrate is administered in an amount of about 10-400 milligrams, from about 15-350 milligrams, from about 20-300 milligrams, from about 50-250 milligrams, from about 75-200 milligrams, from about 100-200 milligrams, or from about 125-175 milligrams. In some embodiments, about 10 milligrams, about 15 milligrams, about 20 milligrams, about 25 milligrams, about 30 milligrams, about 35 milligrams, about 40 milligrams, about 45 milligrams, about 50 milligrams, about 75 milligrams, about 100 milligrams, about 150 milligrams, about 200 milligrams, about 250 milligrams, about 300 milligrams, about 350 milligrams, about 400 milligrams, or about 450 milligrams lithium citrate is administered.

In some embodiments, the source of lithium is lithium orotate administered in an amount of about 10 milligrams to about 450 milligrams. In some embodiments, lithium orotate is administered in an amount of about 10-400 milligrams, from about 15-350 milligrams, from about 20-300 milligrams, from about 50-250 milligrams, from about 75-200 milligrams, from about 100-200 milligrams, or from about 125-175 milligrams. In some embodiments, about 10 milligrams, about 15 milligrams, about 20 milligrams, about 25 milligrams, about 30 milligrams, about 35 milligrams, about 40 milligrams, about 45 milligrams, about 50 milligrams, about 75 milligrams, about 100 milligrams, about 150 milligrams, about 200 milligrams, about 250 milligrams, about 300 milligrams, about 350 milligrams, about 400 milligrams, or about 450 milligrams lithium orotate is administered.

In some embodiments, the commercial source of cesium, rubidium or lithium for use in the present invention is in highly pure form. In some embodiments, the source is 95% pure, 96% pure, 97% pure, 98% pure, 99% pure, 99.5% pure, 99.9% pure, 99,999% pure or greater. Highly pure sources are known to persons of skill in the art and are commercially available. In some embodiments, such sources are non-toxic and pharmaceutically acceptable.

In some embodiments, the one or more alkali metals of the invention are administered substantially together with one or more sources of potassium to prevent a risk of potassium depletion in the individual. In some embodiments, the one or more sources of potassium is elemental potassium, potassium compounds, potassium ions, potassium salts, one or more potassium-rich foods, or combinations thereof. In some embodiments, the potassium-rich foods are selected from the group consisting of banana, raisins, spinach, pumpkin, tomato, broccoli, orange juice, milk, yams, potato, corn, yoghurt, cabbage, salmon, green barley essence, peanut butter, prunes cheese, peach lettuce, celery, ice cream, peas, grapes, pineapple, green beans, asparagus, apple, apricot, rice, onion, strawberries and bread (25% flour) and combinations thereof.

The alkali metals can be administered in a single dose or they can be spread out over several doses in a 24 hour period. In some embodiments, the one or more alkali metals are divided into several doses administered over a 24 hour period. In some embodiments, 2, 3, 4, 5, 6 or more doses are administered. In some embodiments, the one or more alkali metals are administered in a single dose in a 24-hour period.

In some embodiments, the alkali metal sources are the only active agents administered to the individual to promote weight loss or appetite suppression. In other embodiments, additional active agents are administered that promote weight loss or appetite suppression.

In some embodiments the individual to be treated or administered is a mammal. In some embodiments, the individual is a human. The effective amounts as described herein are contemplated for human administration, and can be adjusted as needed to accommodate administration to other species. In some embodiments, the individual is a non-human mammal, such as, for example, a horse, canine (in particular domestic canine animals), feline animals (in particular domestic feline animals) as well as mammals which are produced for meat, such as porcine, bovine and ovine animals. The present invention can be used to prevent excess weight in such animals in order to maximize lean meat production.

The duration of treatment or administration can vary for each individual to be treated/administered. It can be continuous for a period of several days, weeks, months, or years of treatment or can be intermittent where the individual is administered alkali metals for a period of time, followed by a period of time where they are not treated, and then a period of time where treatment resumes as needed to suppress appetite in the individual. For example, in some embodiments, the individual to be treated is administered the alkali metals of the invention daily, every other day, every three days, every four days, 2 days per week 3 days per week, 4 days per week, 5 days per week or 7 days per week. In some embodiments, the individual is administered the alkali metals for 1 week, 2 weeks, 3 weeks, 4 weeks, 1 month, 2 months, 3 months, 4 months, 5 months, 6 months, 7 months, 8 months, 9 months, 10 months, 11 months, 1 year or longer. In some embodiments, the individual is administered a dosage every morning with or after food and taken for two months until the required amount of weight is lost. In some embodiments, individuals who are obese are administered the alkali metal of the invention every day for longer durations of time. In some embodiments, obese individuals are treated for 6 months or longer to achieve the desired weight loss. For purposes of achieving a stimulant effect, the duration of treatment in some embodiments can be very short, limited to a single administration occurring on one day.

The combinations of alkali metal sources are administered substantially together. As used herein "substantially together" refers to administering to an individual more than one alkali metal sources in (i) a single dosage form, or (ii) separate dosage forms or a combination of compositions, such that, they are administered either simultaneously or within a period of time such that the subject receives benefit of the aggregate effects of the separate dosage forms or combination of compositions. In some embodiments, the alkali metal source combinations are administered as a single dose. In some embodiments, separate dosage forms for more than one alkali metal sources are administered within the same 24 hour period. In some embodiments, separate dosage forms for more than one alkali metal sources are administered within the same 12 hour period. In some combinations, separate dosage forms for more than one alkali metal sources are administered within the same 6 hour period. In some embodiments, separate dosage forms for more than one alkali metal sources are administered within the same 3-6 hour period. In some combinations, separate dosage forms for more than one alkali metal sources are administered within the same 1-3 hour period. In some combinations, separate dosage forms for more than one alkali metal sources are administered within the same one hour period. In some embodiments, the appetite suppressant effect achieved by a single dose in the morning is sufficient to halt cravings for food for the remainder of the day. In some embodiments, the weight control composition may be consumed before meals to reduce caloric consumption during meals, or after meals to reduce eating between meals, or consumed in lieu of one or more traditional meals.

In some embodiments, the individual is administered a combination of alkali metals comprising cesium chloride, rubidium chloride and one or more sources of lithium selected from the group consisting of lithium orotate, lithium carbonate, lithium aspartate, lithium citrate and combinations thereof. In some embodiments, the cesium chloride is administered in an amount of about 50 milligrams to about 1900 milligrams or any specific amount or range as described herein, the rubidium chloride is administered in an amount of about 50 milligrams to about 1900 milligrams or any specific amount or range as described herein, the lithium orotate is administered in an amount of about 20 milligrams to about 200 milligrams or any specific amount or range as described herein, the lithium carbonate is administered in an amount of about 10 milligrams to about 450 milligrams or any specific amount or range as described herein, and the lithium aspartate is administered in an amount of about 10 milligrams to about 450 milligrams or any specific amount or range as described herein. In some embodiments, the lithium source includes at least two of: lithium orotate administered in an amount of about 10 milligrams to about 200 milligrams; lithium carbonate administered in an amount of about 10 milligrams to about 450 milligrams; or lithium aspartate administered in an amount of about 10 milligrams to about 450 milligrams. In some embodiments, the lithium orotate is administered in an amount of about 10 milligrams to about 200 milligrams, lithium carbonate is administered in an amount of about 10 milligrams to about 450 milligrams, and lithium aspartate is administered in an amount of about 10 milligrams to about 450 milligrams.

In some embodiments, one or more sources of cesium and lithium are administered to an individual in a single dose, i.e., substantially together. In some embodiments, the source of cesium is cesium chloride and the one or more sources of lithium is selected from the group consisting of lithium orotate, lithium carbonate, lithium citrate, lithium aspartate, and combinations thereof. In some embodiments, the cesium chloride is administered in an amount of about 50 milligrams to about 1900 milligrams or any specific amount or range as described herein. In some embodiments, the lithium orotate is administered in an amount of about 10 milligrams to about 200 milligrams or any specific amount or range as described herein. In some embodiments, the lithium carbonate is administered in an amount of about 10 milligrams to about 450 milligrams or any specific amount or range as described herein. In some embodiments, the lithium citrate is administered in an amount of about 10 milligrams to about 450 milligrams or any specific amount or range as described herein. In some embodiments, the lithium aspartate is administered in an amount of about 10 milligrams to about 450 milligrams or any specific amount or range as described herein. In some embodiments the lithium includes at least two of: lithium orotate administered in an amount of about 10 milligrams to about 200 milligrams or any specific amount or range as described herein; lithium carbonate administered in an amount of about 10 milligrams to about 450 milligrams or any specific amount or range as described herein; or lithium aspartate administered in an amount of about 10 milligrams to about 450 milligrams or any specific amount or range as described herein. In some embodiments, lithium orotate is administered in an amount of about 10 milligrams to about 200 milligrams; lithium carbonate is administered in an amount of about 10 milligrams to about 450 milligrams; and lithium aspartate is administered in an amount of about 10 milligrams to about 450 milligrams.

In some embodiments, one or more sources of rubidium and lithium are administered in a single dose. In some embodiments, the source of rubidium is rubidium chloride and the one or more sources of lithium is selected from the group consisting of lithium orotate, lithium citrate, lithium carbonate and lithium aspartate. In some embodiments, the rubidium chloride is administered in an amount of about 50 milligrams to about 1900 milligrams or any specific amount or range as described herein. In some embodiments, the amount of lithium orotate is administered in an amount of about 10 milligrams to about 200 milligrams or any specific amount or range as described herein. In some embodiments, the lithium citrate is administered in an amount of about 10 milligrams to about 450 milligrams or any specific amount or range as described herein. In some embodiments, the amount of lithium carbonate is administered in an amount of about 10 milligrams to about 450 milligrams or any specific amount or range as described herein. In some embodiments, the lithium aspartate is administered in an amount of about 10 milligrams to about 450 milligrams or any specific amount or range as described herein. In some embodiments, the lithium includes at least two of lithium orotate administered in an amount of about 10 milligrams to about 200 milligrams or any specific amount or range as described herein, lithium carbonate administered in an amount of about 10 milligrams to about 450 milligrams or any specific amount or range as described herein, or lithium aspartate administered in an amount of about 10 milligrams to about 450 milligrams or any specific amount or range as described herein. In some embodiments, lithium orotate is administered in an amount of about 10 milligrams to about 200 milligrams; lithium carbonate is administered in an amount of about 10 milligrams to about 450 milligrams; and lithium aspartate is administered in an amount of about 10 milligrams to about 450 milligrams.

In some embodiments, a combination of 150 milligrams of cesium chloride and 150 milligrams of rubidium chloride is administered. In some embodiments, a combination of 150 milligrams of cesium chloride, 150 milligrams of rubidium chloride and 40 milligrams of lithium carbonate is administered. In other embodiments, a combination of 150 milligrams of cesium chloride, 150 milligrams of rubidium chloride and 40 milligrams of lithium aspartate is administered.

In some embodiments, the invention is directed to weight loss or stimulant compositions useful for suppressing appetite in an individual or promoting a stimulant effect. In some embodiments, the invention is directed to dietary supplement compositions useful for suppressing appetite or promoting a stimulant effect in an individual. In some embodiments, the compositions are pharmaceutical compositions.

In some embodiments, the invention is directed to compositions which are functional foods and/or beverages (such as energy or stimulant drinks). The compositions comprise one or more alkali metals in amounts that are useful in carrying out the methods of the present invention as described herein.

In some embodiments, the weight loss or stimulant compositions of the invention can be prepared in accordance with acceptable pharmaceutical procedures, such as described in *Remington's Pharmaceutical Sciences*, 17th edition, ed. Alfonso R. Gennaro, Mack Publishing Company, Easton, Pa. (1985), herein incorporated by reference in its entirety.

In some embodiments, the compositions of the invention are formulated in unit dosage form for ease of administration and uniformity of dosage. The term "unit dosage form" as used herein refers to physically discrete units suited as unitary dosages for the individuals to be treated. In some embodiments, the compositions are formulated into discrete dosage units each containing a predetermined "unit dosage" or "unit dose" of one or more active compounds calculated to produce the desired effect in association with the required pharmaceutical carrier.

In some embodiments, the compositions have a unit dose or amount of cesium of about 10 milligrams to about 1500 milligrams or any specific amount or range as described herein. In some embodiments, the unit dose or amount of cesium is about 20 milligrams, about 40 milligrams, about 100 milligrams, about 150 milligrams, about 200 milligrams, about 250 milligrams, about 300 milligrams, about 350 milligrams, about 400 milligrams, about 450 milligrams, about 500 milligrams, about 550 milligrams, about 600 milligrams, about 650 milligrams, about 700 milligrams, about 750 milligrams, about 800 milligrams, about 850 milligrams, about 900 milligrams, about 950 milligrams, about 1000 milligrams, about 1050 milligrams, about 1100 milligrams, about 1200 milligrams, about 1250 milligrams, about 1300 milligrams, about 1350 milligrams, about 1400 milligrams, about 1450 milligrams, or about 1500 milligrams.

In some embodiments, the compositions have a unit dose or amount of rubidium of about 10 milligrams to about 1350 milligrams or any specific amount or range as described herein. In some embodiments, the unit dose or amount of rubidium is about 25 milligrams, about 35 milligrams, about 50 milligrams, about 75 milligrams, about 100 milligrams, about 150 milligrams, about 200 milligrams, about 250 milligrams, about 300 milligrams, about 350 milligrams, about 400 milligrams, about 450 milligrams, about 500 milligrams, about 550 milligrams, about 600 milligrams, about 650 milligrams, about 700 milligrams, about 750 milligrams, about 800 milligrams, about 850 milligrams, about 900 milligrams, about 950 milligrams, about 1000 milligrams, about 1050 milligrams, about 1100 milligrams, about 1200 milligrams, about 1250 milligrams, about 1300 milligrams, or about 1350 milligrams.

In some embodiments, the compositions have a unit dose or amount of lithium of about 0.1 milligrams to about 85 milligrams or any specific amount or range as described herein. In some embodiments, the unit dose or amount of lithium is about 1 milligrams, about 1.5 milligrams, about 2 milligrams, about 5 milligrams, about 10 milligrams, about 15 milligrams, about 20 milligrams, about 25 milligrams, about 30 milligrams, about 35 milligrams, about 40 milligrams, about 45 milligrams, about 50 milligrams, about 55 milligrams, about 60 milligrams, about 65 milligrams, about 70 milligrams, about 75 milligrams, about 80 milligrams, or about 85 milligrams.

In some embodiments, the invention is directed to a weight loss composition or combination of compositions taken substantially together comprising: one or more salts of cesium having a combined content in an amount of about 40 milligrams to about 1500 milligrams or any specific amount or range as described herein; one or more salts of rubidium having a combined rubidium content in an amount of about 35 milligrams to about 1350 milligrams or any specific amount or range as described herein; one or more lithium salts having a combined lithium content in an amount of about 0.3 milligrams to about 85 milligrams or any specific amount or range as described herein; and combinations thereof.

In some embodiments, the weight loss or stimulant composition or combination of compositions comprises one or more salts of cesium selected from the group consisting of cesium azide ($CsN_3$), cesium bromide (CsBr), cesium carbonate ($Cs_2CO_3$), cesium chloride (CsCl), cesium chromate ($Cs_2CrO_4$), cesium fluoride (CsF), cesium formate (HCOOCs), cesium iodide (CsI), cesium nitrate ($CsNO_1$), cesium orthovanadate ($Cs_3VO_4$), cesium oxalate (($COOCs)_2$), cesium perchlorate ($CsClO_4$), cesium permanganate ($CsMnO_4$), cesium propionate ($C_2H_5CO_2Cs$) and cesium sulfate ($Cs_2O_4S$). In some embodiments, cesium chloride is present in an amount of about 50 milligrams to about 1900 milligrams.

In some embodiments, the weight loss or stimulant composition or combination of compositions comprises one or more salts of rubidium selected from the group consisting of rubidium acetate ($CH_3CO_2Rb$), rubidium bromide (RbBr), rubidium carbonate ($Rb_2CO_3$), rubidium chloride (RbCl), rubidium chromate ($Rb_2CrO_4$), rubidium fluoride (RbF), rubidium formate ($HCO_2Rb$), rubidium iodide (RbI), rubidium nitrate ($RbNO_3$) and rubidium sulfate ($Rb_2SO_4$). In some embodiments, rubidium chloride is present in an amount of about 100 milligrams to about 1900 milligrams.

In some embodiments, the weight loss or stimulant composition or combination of compositions comprises one or more salts of lithium selected from the group consisting of lithium acetate ($CH_3COOLi$), lithium acetylsalicylate, lithium aspartate, benzoate ($C_6H_5COOLi$), lithium bitartrate, lithium bromide (LiBr), lithium carbonate ($Li_2CO_3$), lithium chloride (LiCl), lithium chromate ($LiCrO_4$), lithium citrate ($Li_3C_6H_5O_7$), lithium fluoride (LiF), lithium gluconate, lithium iodate ($LiIO_3$), lithium metaborate ($LiBO_2$), lithium nitrate ($LiNO_3$), lithium orotate ($LiC_5H_3N_2O_4$), lithium perchlorate ($LiClO_4$), lithium phosphate ($Li_3PO_4$), lithium selenite ($LiH_3(SeO_3)_2$), lithium succinate ($C_4H_5LiO_4$), lithium sulfate ($Li_2SO_4$), and lithium thenoate. In some embodiments, the lithium salt is lithium orotate, lithium carbonate, lithium aspartate, or combinations thereof. In some embodiments, lithium orotate is present in an amount from about 20 milligrams to about 200 milligrams. In some embodiments, lithium carbonate is present in an amount from about 10 milligrams to about 450 milligrams. In some embodiments, lithium aspartate is present in an amount from about 1.0 milligrams to about 450 milligrams.

In some embodiments, the weight loss or stimulant composition or combination of compositions includes at least two of: lithium orotate in an amount of about 20 milligrams to about 200 milligrams; lithium carbonate in an amount of about 20 milligrams to about 450 milligrams, or lithium aspartate in an amount of about 20 milligrams to about 450 milligrams.

In some embodiments, the weight kiss or stimulant composition or combination of compositions includes lithium orotate in an amount of about 20 milligrams to about 200 milligrams; lithium carbonate in an amount of about 10 milligrams to about 450 milligrams, and lithium aspartate in an amount of about 10 milligrams to about 450 milligrams.

Pharmaceutically acceptable carriers are those that are compatible with the other ingredients in the formulation and biologically acceptable. The alkali metal can be provided in combination with a pharmaceutically acceptable carrier or diluent. Suitable carriers and/or diluents are well known in the art and include pharmaceutical grade starch, mannitol, lactose, magnesium stearate, sodium saccharin, talcum, cellulose, glucose, sucrose, (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration). The alkali metals can also be administered pure in sachets that have to be added to a glass of water and then drunk.

The compositions according to the invention for use in the aforementioned methods may be administered by any convenient method, for example by oral (including by inhalation), parenteral, mucosal (e.g. buccal, sublingual, nasal), rectal, subcutaneous or transdermal administration and the compositions adapted accordingly.

In some embodiments, the weight loss or stimulant composition is suitable for oral administration. In some embodiments, the weight loss composition is a tablet, capsule, pill, dragee, suspension, lozenge, emulsion, aqueous solution, liquid, gel, or syrup. In some embodiments, the compositions can be delivered in the form of functional foods and/or beverages (such as energy or stimulant drinks), as well as in the form of various dietary supplements.

A liquid formulation or liquid composition will generally comprise a suspension or solution of the one or more alkali metals or salts in a suitable aqueous or non-aqueous liquid carrier(s), for example, water, ethanol, glycerine, polyethylene glycol or an oil. In some embodiments, the composition formulation or composition may also contain a suspending agent, preservative, flavoring or coloring agent.

In some embodiments, the weight loss or stimulant composition is in the form of a beverage or energy drink, which may further comprise vitamins, minerals, electrolytes and combinations thereof.

In some embodiments, the beverage or energy drink comprises one or more of the following alkali metals and amounts: a source of rubidium having a total rubidium content in an amount of about 35 milligrams to about 1350 milligrams or any specific amount of rubidium or range as described herein, a source of cesium having a total cesium content in an amount of about 40 milligrams to about 1500 milligrams or any specific amount of cesium or range as described herein, and a source of lithium having a total lithium content in an amount of about 0.3 milligrams to about 85 milligrams or any specific amount of lithium or range as described herein.

In some embodiments, the beverage or energy drink comprises one or more of the following alkali metals and amounts: rubidium chloride in an amount of about 50 milligrams to about 1900 milligrams or any specific amount or range of rubidium chloride as described herein, cesium chloride in an amount of about 50 milligrams to about 1900 milligrams or any specific amount or range of cesium chloride as described herein, and one or more of lithium orotate, lithium aspartate, and lithium carbonate in an amount of about 20 milligrams to about 200 milligrams or any specific amount or range of lithium orotate, lithium aspartate, and lithium carbonate as described herein. In some embodiments, electrolytes such as potassium, for example, are included, which in correct physiological quantities can increase the efficiency of the body to utilize glycogen and improve muscular activities. In some embodiments, the electrolytes comprise sodium, potassium, chloride, magnesium, bicarbonate or a combination thereof. In some embodiments, the source of potassium in the beverage or energy drink compositions is potassium chloride. In some embodiments, potassium other than in the form of potassium chloride, such as potassium citrate, gluconate, carbonate or phosphate, may induce potassium deficiency and alkalosis. A depletion of potassium can lead to a decrease in action potential of muscle and can also cause metabolic alkalosis. Certain beverage or energy drink embodiments overcome this problem.

In some embodiments, carbohydrates can be added, including sucrose, glucose, citrate or a combination thereof. In some embodiments, one or more carbohydrates are added with one or more electrolytes. In some embodiments, the unpleasant taste of electrolytes in drinks can be masked by carefully balancing the relative ratios of the electrolytes.

In some embodiments, the beverage or energy drink can comprise a combination of water, one or more alkali metals, carbohydrates, and electrolytes, such as sodium, potassium, chloride, magnesium and/or bicarbonate. In some embodiments, the beverage or energy drink can further comprise one or more of high fructose corn syrup, artificial colors and flavors. In some embodiments, the carbohydrate is glucose, fructose, dextrose, sucrose or a combination thereof. In some embodiments, the beverage or energy drink comprises taurine and/or glucuronolactone.

In some embodiments, the energy drink comprises a combination of disodium hydrogen phosphate ($Na_2HPO_4.12H_2O$), sucrose, dextrose, rubidium chloride, potassium chloride, magnesium sulfate, sodium citrate, sodium acid phosphate, ascorbic acid, pyridoxine hydrochloride, citric acid, and sodium chloride. In some embodiments, artificial sweeteners, colorings, vitamins, minerals, preservatives and combinations thereof may be incorporated.

When in powder form, the composition of one or more alkali base metals may be provided as small crystals. In some embodiments, the powder composition may be prepared by simply admixing the appropriate reactant ingredients and packaging them in conventional beverage containers used for such purposes. In some embodiments, the liquid carrier used on-demand to form the fluid beverage may be distilled, deionized, carbonated, or mineral water, and the liquid may also contain a small amount of nonglucose or low glycemic index sweetener (such as aspartame or sucralose) to impart a pleasant sweet taste to the prepared beverage. In some embodiments, such a fluid beverage will have a total caloric load not to exceed 60 kcal per serving, and optionally is flavored with one or more natural and artificial sweeteners, either individually or in combination, in their usual proportions. The resulting fluid beverage can be initially preserved by pasteurization or cold sterilization. In some embodiments, the beverage is consumed at an average volume intake of less than one liter per day.

In some embodiments, the dry composition (of chosen ingredients) can be mixed at will with a very small amount of water (for example, less than 30 ml) to produce a mixture which may later be diluted to provide multiple units in the proper dose amounts, or can be poured into capsule form, designed for optimum portability in situations requiring little weight or baggage.

It is to be appreciated that the dry composition of one or more alkali base metals is water soluble which allows a host of delivery options.

In addition, the weight loss or stimulant composition may be kept as a dry powder mixture (for example in sachets) for an indefinite time period without degradation. Then, at a chosen later time, the dry powder can be combined with water or another aqueous based liquid, and optionally a small amount of non-glucose or low glycemic index sweetener such as aspartame or sucralose to impart a pleasant sweet taste for the beverage. In some embodiments, the beverage will have a total caloric value not to exceed 60 kcal per serving, after being properly constituted as a ready to drink fluid.

Optionally, the dry particle admixture may be flavored with one or more natural and/or artificial favoring aids or sweeteners, either individually or in combination, in their usual proportions. The powder can then be packaged in individual moisture and tamper-resistant packaging available commercially for such purposes.

A composition in the form of a tablet can be prepared using any suitable pharmaceutical carrier(s) routinely used for preparing solid formulations. Examples of such carriers include magnesium stearate, starch, lactose, sucrose and microcrystalline cellulose.

A composition in the form of a capsule can be prepared using routine encapsulation procedures. For example, powders, granules or pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

In some embodiments, the alkali metals are in powder form and are filled in a capsule. In some embodiments, pharmaceutical excipients are added to the powder. In some embodiments, potassium is added in amounts ranging from about 150 milligrams to about 5000 milligrams. Pharmaceutical excipients can be added to the alkali metals to counteract any discomfort of the alkali properties when ingested, such as, for example, gelatin, or mask any unpleasant taste of the composition.

In some embodiments, the weight loss or stimulant compositions of the invention can additionally be formulated with vitamins and minerals, including to compensate for any loss thereof due to a reduced food intake by the individual. In some embodiments, a multivitamin and mineral supplement is administered separately from the pharmaceutical composition. Multivitamin and mineral supplements are well known. Such supplements typically contain vitamins A, B1, B2, B6, B12, C, D, E, folic acid, calcium, iron, magnesium and zinc. Amino acids may also be included to supplement the daily protein requirement.

Typical parenteral compositions consist of a solution or suspension of the alkali metal in a sterile aqueous or non-aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal or oral administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a pharmaceutically acceptable propellant. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin. Compositions for rectal or vaginal administration are conveniently in the form of suppositories (containing a conventional suppository base such as cocoa butter), pessaries, vaginal tabs, foams or enemas. Compositions suitable for transdermal administration include ointments, gels, patches and injections including powder injections.

The present invention may be better understood by reference to the following non-limiting Examples, which are provided as exemplary of the invention. The following examples are presented in order to more fully illustrate some embodiments of the invention. They should in no way be construed, however, as limiting the broad scope of the invention.

EXAMPLES

Example 1

A 100 kg man was administered a pharmaceutical composition of the invention. Cesium chloride (1.50 milligrams), rubidium chloride (1.50 milligrams) and lithium aspartate (40 milligrams) together were dissolved in one glass of water and ingested in the morning daily over a two month period. The individual experienced a light tingling around the mouth and a strong stimulation effect in the brain in a few minutes after administration. Weight loss of 1.0 kilograms also was achieved. Alternatively and over two other periods of two months, the individual alkali metals, cesium chloride (300 milligrams) and rubidium chloride (300 milligrams), were dissolved in water and ingested separately rather than in combination, and the individual alkali metals administered separately worked as well and with the same sensation.

Example 2

Beverage Composition

Rubidium Chloride 300 mg
Potassium Chloride: 300 mg.
Diluted in 150 ml of water

If desired, a flavoring agent such as TRUSIL LEMON ELITE (the trade name of a commercial lemon flavoring agent supplied by Bush, Boake & Allan), may be incorporated in the mixture to provide a particularly pleasant flavor on the palate. Artificial sweeteners, colorings and preservatives may likewise be incorporated.

Example 3

Beverage Composition

A first mixture (mixture A) was prepared by blending 500 mg of disodium hydrogen phosphate ($Na_2HPO_4.12H_2O$) with 5 g of sucrose and 3 g of dextrose.

A second mixture (mixture B) was prepared by blending together the following ingredients in the stated amounts:
Rubidium Chloride: 300 mg
Potassium Chloride: 300 mg
Magnesium Sulfate: 150 mg
Sodium Citrate: 120 mg
Sodium Acid Phosphate: 110 mg
Ascorbic Acid: 100.0 mg
Pyridoxine Hydrochloride: 25.0 mg
Citric Acid: 450 mg
Sodium Chloride: 70 mg The two mixtures were then blended together and milled to 100 mesh to form a drink concentrate.

If desired, a flavoring agent such as TRUSIL LEMON ELITE (the trade name of a commercial lemon flavoring agent supplied by Bush, Boake & Allan), may be incorporated in the mixture to provide a particularly pleasant flavor on the palate. Artificial sweeteners, colorings and preservatives may likewise be incorporated.

Example 4

The therapeutic efficacy of a composition in accordance with the present invention has been tested herein.

These trials were not undertaken to lose weight as quickly as possible but rather they were undertaken with the recommendation by doctors to the subject(s) not to lose weight too quickly and to eat potassium rich foods, especially at night, instead of junk food.

As such, the aim of these trials was to have the subjects lose weight and stop the cravings for junk food with the aid of the compositions of this invention and use the enhanced energy and stimulation supplied from the compositions to change eating habits away from junk food thereby facilitating weight loss.

During a first trial, a subject was administered 300 mg of cesium chloride once per day in a glass of water every morning. The first trial lasted two months (61 days) and the subject (100 kg) lost ten kilograms during this time period, as follows:

| Day | Weight (kg) |
| --- | --- |
| 1-9 | 100 |
| 10-13 | 99 |
| 14-15 | 98 |
| 16-23 | 97 |
| 24-34 | 96 |
| 35-41 | 95 |
| 42-47 | 94 |
| 48-52 | 93 |
| 53-55 | 92 |
| 56-58 | 91 |
| 59-61 | 90 |

Example 5

In a second trial, the subject was administered 120 mg of lithium carbonate once per day with a glass of water every morning for two months (59 days). The subject reported after two weeks the stress of trying to diminish junk food intake was reduced. Weight loss resulted, as follows:

| Day | Weight (kg) |
| --- | --- |
| 1-14 | 100 |
| 15-19 | 99 |
| 20-27 | 98 |
| 28-35 | 97 |
| 36-39 | 96 |
| 40-46 | 95 |
| 47-52 | 94 |
| 53-57 | 93 |
| 58-59 | 92 |

Example 6

In a third trial, the subject was administered 40 mg of lithium carbonate with a glass of water every morning for two months. The subject reported that the most difficult aspect was to stop the craving for junk food in the evening and the late afternoon. The subject also reported that there was not the feeling of stimulation as in the first trial, but that after two weeks the stress of trying to reduce junk food intake was reduced. Weight loss also resulted.

| Day | Weight (kg) |
|---|---|
| 1-15 | 100 |
| 16-25 | 99 |
| 26-34 | 98 |
| 35-41 | 97 |
| 42-48 | 96 |
| 49-53 | 95 |
| 54-57 | 94 |
| 58-60 | 93 |
| 61 | 92 |

Example 7

In a fourth trial, the subject was administered 300 mg of rubidium chloride once per once day in a glass of water in the morning. This trial lasted two months (61 days), and the subject lost ten kilograms during this time period. The most difficult aspect reported was the urge to eat junk food for dinner and the cravings in the evening, which contributed to poor weight loss at the beginning of the trial (an option for people who cannot stop eating junk food at night would be to split the dosage and take half in the morning and half late in the afternoon or increase the dosage to 200 mg in the morning and 200 mg in the late afternoon). Weight loss resulted, as follows:

| Day | Weight (kg) |
|---|---|
| 1-10 | 102 |
| 11-15 | 101 |
| 16-23 | 100 |
| 24-29 | 99 |
| 30-35 | 98 |
| 36-40 | 97 |
| 41-45 | 96 |
| 46-50 | 95 |
| 51-54 | 94 |
| 55-59 | 93 |
| 60-61 | 92 |

Example 8

In a fifth trial, the subject was administered 150 mg of rubidium chloride, 150 mg cesium chloride, and 40 mg of lithium carbonate once per day together in a glass of water in the morning. This trial lasted two months (61 days) and the subject lost ten kilograms during this time period. The most difficult aspect reported by the subject was the craving for junk food for dinner or late in the afternoon. This contributed to the little weight loss early in the study. After two weeks, the subject reported less stress and less craving for junk food as compared to the first trial (for people who cannot stop eating at night, one solution would be to split the dosage and take half in the morning and half late in the afternoon, or increase the dosage to 100 mg of rubidium chloride, 100 mg of cesium chloride, and 20 mg of lithium carbonate in the morning and again in the late afternoon). In this study, weight loss resulted, as follows:

| Day | Weight (kg) |
|---|---|
| 1-11 | 100 |
| 12-15 | 99 |
| 16-19 | 98 |
| 20-23 | 97 |
| 24-26 | 96 |
| 27-28 | 95 |
| 29-35 | 94 |
| 36-42 | 93 |
| 43-47 | 92 |
| 48-55 | 91 |
| 56-61 | 90 |

Example 9

In further trials, the subject was administered lithium salts—lithium orotate, lithium aspartate, and lithium citrate (40 mg) with a glass of water in the morning. The subject reported similar cravings as noted above. The subject reported that there was not the feeling of stimulation as in the first and fourth trials, but that after two weeks, the stress of trying to diminish junk food intake decreased. Weight loss was recorded.

Example 10

In a blind trial with two subjects, a female subject (66 kg) was administered 300 mg of rubidium chloride once per day in a glass of water in the morning for two months (61 days). The second subject was a male (98 kg) who was administered a placebo of powdered sugar once per day in a glass of water in the morning during the same two months.

The male subject did not lose weight over the two month trial but the female stated "the stimulation from the medication she took was very, very strong" and she had more get-up-and go and less craving for junk food than normal even after the first day. She also stated she had much more energy than before and was much more active during the day with the "medication" The trial was undertaken with the recommendation by doctors not to lose weight too quickly and to eat potassium rich foods, especially at night, instead of junk food. The most difficult aspect reported by the subject was to stop eating junk food for dinner and to stop the craving for junk food in the evening, which is believed to be the reason for little weight loss at the beginning of the trial (a proposed solution for people who cannot stop eating at night would be to split the dosage of the 300 mg of rubidium chloride and take half in the morning and half late in the afternoon).

The aim of this trial was to have the subject lose weight and stop the craving for junk food with the aid of the composition. The enhanced energy and stimulation supplied from the composition that was tested to determine if it prompted a change in eating habits away from junk food, thereby facilitated weight loss. Both subjects stated there was a higher craving for junk food for them in the afternoon and evening.

The trial lasted two months and the male subject lost no weight and found the powdered sugar caused no stimulation, while the female subject lost 6.5 kilograms during this time period, as follows:

| Day | Weight (kg) |
|---|---|
| 1-5 | 66 |
| 6-9 | 65.5 |
| 10-12 | 65 |

-continued

| Day | Weight (kg) |
|---|---|
| 13-18 | 64 |
| 19-28 | 63 |
| 29-30 | 64 |
| 31-32 | 63.5 |
| 33-34 | 63 |
| 35-43 | 62 |
| 44-51 | 61 |
| 52-55 | 60.5 |
| 56-59 | 60 |
| 60-61 | 59.5 |

While there have been shown and described what are presently believed to be certain embodiments of the present invention, those skilled in the art will realize that other and further embodiments can be made without departing from the spirit and scope of the invention described in this application, and this application includes all such modifications that are within the intended scope of the claims set forth herein.

What is claimed is:

1. A method of suppressing appetite in an individual in need thereof, comprising orally administering to the individual per 24 hour period an effective amount of one or more sources of cesium,
wherein the one or more sources of cesium administered has a total cesium content in an amount of about 40 milligrams to 1500 milligrams.

2. The method of claim 1, wherein the source of cesium is one or more salts of cesium.

3. The method of claim 2, wherein the one or more salts of cesium is selected from the group consisting of cesium azide ($CsN_3$), cesium bromide (CsBr), cesium carbonate ($Cs_2CO_3$), cesium chloride (CsCl), cesium chromate ($Cs_2CrO_4$), cesium fluoride (CsF), cesium formate (HCOOCs), cesium iodide (CsI), cesium nitrate ($CsNO_3$), cesium orthovanadate ($Cs_3VO_4$), cesium oxalate (($COOCs)_2$), cesium perchlorate ($CsClO_4$), cesium permanganate ($CsMnO_4$), cesium propionate ($C_2H_5CO_2Cs$) and cesium sulfate ($Cs_2O_4S$).

4. The method of claim 1, further comprising one or more sources of potassium administered substantially together with the one or more cesium sources.

5. The method of claim 1, wherein the one or more sources of cesium is administered as a single dose.

6. The method of claim 5, wherein
the one or more sources of cesium is cesium chloride.

7. The method of claim 6, wherein cesium chloride is administered in an amount of about 50 milligrams to 1500 milligrams.

8. The method of claim 1, wherein the one or more sources of cesium has a total cesium content of about 40-1000 milligrams.

9. The method of claim 1, wherein the one or more sources of cesium has a total cesium content of about 40-750 milligrams.

10. The method of claim 1, wherein the one or more sources of cesium has a total cesium content of about 60-500 milligrams.

11. The method of claim 1, wherein the one or more sources of cesium has a total cesium content of about 80-400 milligrams.

12. The method of claim 1, wherein the one or more sources of cesium has a total cesium content of about 100-300 milligrams.

13. The method of claim 1, wherein the one or more sources of cesium has a total cesium content of about 150-250 milligrams.

14. The method of claim 1, wherein the method comprises administration of a beverage composition comprising:
i) water;
ii) a source of cesium having a total cesium content in an amount of about 40 milligrams to 1500 milligrams;
iii) an electrolyte comprising sodium, potassium, chloride, magnesium, bicarbonate or a combination thereof;
iv) a carbohydrate selected from the group consisting of glucose, fructose, dextrose, sucrose and a combination thereof; and
v) optionally one or more of high fructose corn syrup, artificial colors and flavors.

15. A method of suppressing appetite in an individual in need thereof, comprising orally administering to the individual per 24 hour period:
300 mg of a rubidium salt and 300 mg of a cesium salt, and optionally, 300 mg of a potassium salt; or
150 mg of a rubidium salt and 150 mg of a cesium salt.

16. A beverage composition comprising:
(i) Water;
(ii) about 500 mg disodium hydrogen phosphate;
(iii) about 5 g sucrose;
(iv) about 3 g dextrose;
(v) about 300 mg of a potassium salt selected from the group consisting of potassium chloride, potassium citrate, potassium gluconate, potassium carbonate, and potassium phosphate;
(vi) about 150 mg magnesium sulfate;
(vii) about 120 mg sodium citrate;
(viii) about 110 mg sodium acid phosphate;
(ix) about 100 mg ascorbic acid;
(x) about 25 mg pyridoxine hydrochloride;
(xi) about 450 mg citric acid; and
(xii) about 70 mg sodium chloride;
wherein said composition further comprises one or more of the following:
about 300 mg of a rubidium salt selected from the group consisting of rubidium acetate ($CH_3CO_2Rb$), rubidium bromide (RbBr), rubidium carbonate ($Rb_2CO_3$), rubidium chloride (RbCl), rubidium chromate ($Rb_2CrO_4$), rubidium fluoride (RbF), rubidium formate ($HCO_2Rb$), rubidium iodide (RbI), rubidium nitrate ($RbNO_3$) and rubidium sulfate ($Rb_2SO_4$); and
about 300 mg a cesium salt selected from the group consisting of cesium azide ($CsN_3$), cesium bromide (CsBr), cesium carbonate ($Cs_2CO_3$), cesium chloride (CsCl), cesium chromate ($Cs_2CrO_4$), cesium fluoride (CsF), cesium formate (HCOOCs), cesium iodide (CsI), cesium nitrate ($CsNO_3$), cesium orthovanadate ($Cs_3VO_4$), cesium oxalate (($COOCs)_2$), cesium perchlorate ($CsClO_4$), cesium permanganate ($CsMnO_4$), cesium propionate ($C_2H_5CO_2Cs$) and cesium sulfate ($Cs_2O_4S$); and
wherein said composition optionally includes a flavoring agent.

17. The composition of claim 16, wherein the composition comprises:
(i) water;
(ii) 500 mg disodium hydrogen phosphate;
(iii) 5 g sucrose;
(iv) 3 g dextrose;

(v) 300 mg of a potassium salt selected from the group consisting of potassium chloride, potassium citrate, potassium gluconate, potassium carbonate, and potassium phosphate;
(vi) 150 mg magnesium sulfate;
(vii) 120 mg sodium citrate;
(viii) 110 mg sodium acid phosphate;
(ix) 100 mg ascorbic acid;
(x) 25 mg pyridoxine hydrochloride;
(xi) 450 mg citric acid;
(xii) 70 mg sodium chloride; and
(xiii) 300 mg of a rubidium salt selected from the group consisting of rubidium acetate ($CH_3CO_2Rb$), rubidium bromide (RbBr), rubidium carbonate ($Rb_2CO_3$), rubidium chloride (RbCl), rubidium chromate ($Rb_2CrO_4$), rubidium fluoride (RbF), rubidium formate ($HCO_2Rb$), rubidium iodide (RbI), rubidium nitrate ($RbNO_3$) and rubidium sulfate ($Rb_2SO_4$); and
wherein said composition optionally includes a flavoring agent.

18. The composition of claim 17, wherein said rubidium salt is rubidium chloride (RbCl) and wherein said potassium salt is potassium chloride (KCl).

19. The composition of claim 16, wherein said cesium salt is cesium chloride (CsCl) and wherein said potassium salt is potassium chloride (KCl).

* * * * *